United States Patent [19]

Silverstein et al.

[11] Patent Number: 5,422,372
[45] Date of Patent: Jun. 6, 1995

[54] METHOD OF INCREASING INTRACELLULAR ACCUMULATION OF HYDROPHILIC ANIONIC AGENTS USING GEMFIBRIZOL

[75] Inventors: Samuel C. Silverstein, New York; Harold C. Neu, Hastings-on-Hudson; Charles Cao, New York, all of N.Y.

[73] Assignee: The Trustees Of Columbia University In The City Of New York, New York, N.Y.

[21] Appl. No.: 77,755

[22] Filed: Jun. 15, 1993

Related U.S. Application Data

[63] Continuation of Ser. No. 746,961, Aug. 19, 1991, abandoned, which is a continuation-in-part of Ser. No. 508,009, Apr. 10, 1990, abandoned.

[51] Int. Cl.⁶ .............................................. A61K 31/19
[52] U.S. Cl. ...................................................... 514/571
[58] Field of Search ......................................... 514/571

[56] References Cited

U.S. PATENT DOCUMENTS 4,859,703  8/1989  Kraus ................................. 514/543
4,891,220  1/1990  Donzis ................................. 424/88

OTHER PUBLICATIONS

Merck Index 10th Ed. 4246 (1983).
Merck Index, (1983), Edition 10, Merck & Co., Inc., Rahway, N.J., U.S.A., (*gemfibrozil*, at monograph number 4246), p. 626.
Steinberg, T. H., et al., *Journal of Cell Biology*, 1987, vol. 105, No. 6, pp. 2695–2702.
Steinberg, T. H., et al., *Journal of Cell Biology*, 1988, vol. 107, No. 3 pp. 887–896.
Di Virgilio, F., et al., *The Biochemical Journal*, 1988, vol. 256, No. 3, pp. 959–963.
Endicott, J. A., et al., *Annual Review of Biochemistry*, 1989, vol. 58, pp. 137–171.
Slovak, M. L., et al., *Leukemia*, 1988, vol. 2, No. 6, pp. 453–458.
Lowry, O. H., et al., *The Journal of Biological Chemistry*, 1951, vol. 193, pp. 265–275.
Buisman, H. P., et al., *Proceedings of the National Academy of Sciences*, USA, 1988, vol. 85, No. 21, pp. 7988–7992.
Portnoy, D. A., et al., *Journal of Experimental Medicine*, 1988, vol. 167, No. 4, pp. 1459–1471.
Cao, C., et al., *Clinical Research*, 1990, vol. 38, No. 2, p. 364A.

*Primary Examiner*—Raymond Henley, III
*Assistant Examiner*—Russell Travers
*Attorney, Agent, or Firm*—John P. White

[57] ABSTRACT

This invention provides an improved therapeutic method which comprises administering to a mammal a therapeutic agent and 5-(2,5-dimethylphenoxy)-2,2-dimethyl-pentanoic acid, or a structural analog thereof, in an amount effective to improve the efficacy of the therapeutic agent. Also provided by this invention is an improved therapeutic method which comprises administering to a mammal a therapeutic agent and 5-(2,5-dimethylphenoxy)-2,2-dimethyl-pentanoic acid, or a structural analog thereof, in an amount effective to improve the efficacy of the therapeutic agent. Further provided by this invention is a method of treating an intracellular bacterial infection which comprises contacting the infected cell with an effective amount of a therapeutic agent and with an effective amount of 5-(2,5-dimethylphenoxy)-2,2-dimethyl-pentanoic acid, or a structural analog therof, effective to treat an intracellular bacterial infection. A pharmaceutical composition is further provided by this invention wherein the composition comprises a therapeutic agent and 5-(2,5-dimethylphenoxy)-2,2-dimethylpentanoic acid, or a structural analog thereof, and a pharmaceutically acceptable carrier.

24 Claims, 9 Drawing Sheets

METHOD OF INCREASING INTRACELLULAR ACCUMULATION OF HYDROPHILIC ANIONIC AGENTS USING GEMFIBRIZOL

The invention described herein was made in the course of work under Grant No. AI 20516 and AI 26686-02-PJ3 from the United States Public Health Service. The United States Government has certain rights in this invention.

This application is a continuation of U.S. Ser. No. 07/746,961, filed Aug. 19, 1991, now abandoned; which is a continuation-in-part of U.S. Ser. No. 07/508,009, filed Apr. 10, 1990, now abandoned, the contents of which are hereby incorporated by reference into the present disclosure.

BACKGROUND OF THE INVENTION

Throughout this application various publications are referenced to by arabic numerals within parenthesis. Full bibliographic citations for these references may be found at the end of the specification immediately preceding the claims. The disclosures for these publications in their entireties are hereby incorporated by reference into this application to more fully describe the state of the art to which this invention pertains.

Mouse peritoneal macrophages and cells of the J774 macrophage-like cell line express organic transporters that remove Lucifer Yellow and other water soluble anionic dyes from the cells' cytoplasmic matrix. (1) Lucifer Yellow is transported from the cytoplasmic matrix into endosomes, delivered from endosome to lysosomes, and also secreted into the extracellular medium. (1,2) Within 30 minutes after the dye is introduced into the cytosol by ATP-mediated permeabilization of the plasma membrane, 80–85% of the dye is secreted by the cells into the medium; the dye remaining in the cells is present within the endocytic compartment and ultimately is transferred to lysosomes. Probenecid and sulfinpyrazone inhibit both intracellular sequestration and secretion of Lucifer Yellow. Although the endogenous substrates for these organic anion transporters are not known, many metabolites and secreted mediators, including bilirubin, glutathione, prostaglandins, and leukotrienes, are substrates for organic anion transporters in various polarized epithelia.

Many antibiotics are organic anions; indeed, probenecid was developed specifically to inhibit the secretion of penicillin G by organic anion transporters of the renal tubular epithelium.

SUMMARY OF THE INVENTION

This invention provides a method to enhance intracellular accumulation in mammalian cells of a hydrophilic, anionic therapeutic agent which cannot normally accumulate in such cells which comprises contacting the cells with the therapeutic agent and with 5-(2,5-dimethylphenoxy)-2,2-dimethylpentanoic acid, or a structural analog thereof, in an amount effective to block transport of the therapeutic agent from the cells causing intracellular accumulation of the therapeutic agent in the cells.

A pharmaceutical composition is further provided by this invention wherein the composition comprises a therapeutic agent and 5-(2,5-dimethylphenoxy)-2,2-dimethylpentanoic acid, or a structural analog thereof, and a pharmaceutically acceptable carrier.

Also provided by this invention is an improved therapeutic method which comprises administering to a mammal a therapeutic agent and 5-(2,5-dimethylphenoxy)-2,2-dimethylpentanoic acid, or a structural analog thereof, in an amount effective to improve the efficacy of the therapeutic agent.

Further provided by this invention is a method of treating an intracellular bacterial infection which comprises contacting the infected cell with an effective amount of a therapeutic agent and with an effective amount of 5-(2,5-dimethylphenoxy)-2,2-dimethyl-pentanoic acid, or a structural analog therof, effective to treat an intracellular bacterial infection.

BRIEF DESCRIPTION OF THE FIGURES

FIG. 1. Penicillin G competes with Lucifer Yellow for transport via organic anion transporters. J774 cells were incubated in PBS containing 0.5 mg/ml Lucifer Yellow and 5 mM ATP with probenecid, penicillin G, gluconic acid, pyrazinamide or paraaminohippurate as indicated. At the end of the 15 minutes incubation, the cells were washed, lysed in Triton X-100, and fluorescence was quantitated. The results show averages of three separate experiments each done in triplicate, and their standard errors. Analysis of variance: **$p<0.01$.

FIG. 2. Probenecid-sensitive Penicillin G efflux from J774 macrophages. J774 cells were loaded with [$^4$C] penicillin G by ATP-permeabilization. The cells were then incubated in DMEM in the presence (filled circles) or absence (open circles) of 10 mM probenecid. At intervals, the cells were washed, lysed in Triton X-100, and radiolabel was quantitated as described. The results show averages of three separate experiments each done in triplicates, and their standard errors.

FIG. 3. Probenecid reversibly increased intracellular retention of norfloxacin. J774 cells were incubated with [$^3$H] norfloxacin in the presence (filled circles) or absence (open circles) of 10 mM probenecid for various times. Some samples in probenecid were washed and reincubated in fresh medium (triangles). At the end of the incubation, the cells were washed, then lysed and radiolabled norfloxacin counted in a scintillation counter. The results show averages of three or more separate experiments each done in triplicates, and their standard errors.

DETAILED DESCRIPTION OF THE INVENTION

This invention provides a method to enhance intracellular accumulation in mammalian cells of a hydrophilic, anionic therapeutic agent which cannot normally accumulate in such cells which comprises contacting the cells with the therapeutic agent and with 5-(2,5-dimethylphenoxy)-2,2-dimethylpentanoic acid, or a structural analog thereof, in an amount effective to block transport of the therapeutic agent from the cells causing intracellular accumulation of the therapeutic agent in the cells. In one embodiment of this invention, the hydrophilic, anionic therapeutic agent which cannot normally accumulate in the cells is an antibiotic. For the purposes of this invention, the antibiotic is an antibiotic selected from the group consisting of penicillins, cephalosporins, or quinolones. In the most preferred embodiment, the quinolone is norfloxacin.

The contacting of the cell with the therapeutic agent and with the 5-(2,5-dimethylphenoxy)-2,2-dimethylpentanoic acid, or a structural analog thereof, is sequential or simultaneous with respect to each other.

Also provided by this invention is an improved therapeutic method which comprises administering to a mammal a therapeutic agent and 5-(2,5-dimethylphenoxy)-2,2-dimethylpentanoic acid, or a structural analog thereof, in an amount effective to improve the efficacy of the therapeutic agent. For the purposes of this invention, the mammal may be, but is not limited to a human. In one embodiment of this invention, the therapeutic agent is an antibiotic, such as an antibiotic selected from the group consisting of penicillins, cephalosporins, or quinolones. In the most preferred embodiment, the quinolone is norfloxacin.

In the method of this invention, administration of the therapeutic agent and the 5-(2,5-dimethylphenoxy)-2,2-dimethylpentanoic acid, or a structural analog thereof, is sequential or simultaneous with respect to each other.

A pharmaceutical composition is further provided by this invention wherein the composition comprises a therapeutic agent and 5-(2,5-dimethylphenoxy)-2,2-dimethylpentanoic acid, or a structural analog thereof, and a pharmaceutically acceptable carrier. In one embodiment of this invention, the therapeutic agent may be, but is not limited to an antibiotic, such as an antibiotic selected from the group consisting of penicillins, cephalosporins, or quinolones. In the preferred embodiment of this invention, the quinolone is norfloxacin.

Further provided by this invention is a method of treating an intracellular bacterial infection which comprises contacting the infected cell with an effective amount of a therapeutic agent and with an effective amount of 5-(2,5-dimethylphenoxy)-2,2-dimethyl-pentanoic acid, or a structural analog therof, effective to treat an intracellular bacterial infection. For the purposes of this invention, the therapeutic agent may be, but is not limited to an antibiotic, such as an antibiotic selected from the group consisting of penicillins, cephalosporins, or quinolones. In the most preferred embodiment of this invention, the antibiotic is a quinolone, e.g., norfloxacin.

The contacting of the infected cell with the therapeutic agent and with the 5-(2,5-dimethylphenoxy)-2,2-dimethylpentanoic acid, or a structural analog thereof, is sequential or simultaneous, with respect to each other.

For the purposes of this invention the intracellular bacterial infection includes, but is not limited to an infection by Listeria, Tuberculosis, Mycoplasma, Legionella, Leprosy, Brucella or Salmonella.

As used herein, the term accumulation is defined as the total concentration of the therapeutic agent within the cell and thus includes that which is located and/or sequestered within intracellular organelles, for example, vacuoles and phagosomes. For the purposes of this invention, mammalian cells includes all cell types, including, but not limited to macrophages, nerve cells, neuroblastoma cells, epithelial cells and white blood cells.

Examples of therapeutic agents useful in the practice of this invention include, but are not limited to antibiotics, such as beta-lactam antibiotics, for example, penicillins, cephalosporins and streptomycin, quinoline antibiotics such as ciprofloxacin, norfloxacin, and hydrophilic, antiviral agents, such as interferon or its hydrophilic, anionic form thereof, and cancer chemotherapeutic agents, for example, doxorubicin hydrochloride, cisplatin and platinum, diammine [1,1-cyclobutane-decarboxylate(2-)-0,0'], or the anionic, hydrophilic form thereof.

The method of this invention may be practiced in vitro or in vivo. If the method is practiced in vitro, contacting may be effected by incubating the cells with the agent and with the 5-(2,5-dimethylphenoxy)-2,2-dimethylpentanoic acid, or a structural analog thereof. The concentration of the therapeutic agent is effective for its intended purpose and thus, will vary with the cell and purpose of the contacting.

Another factor in determining the effective amount of the therapeutic agent the amount or analog of 5-(2,5-dimethylphenoxy)-2,2-dimethylpentanoic acid.

The methods of the present invention are intended for the treatment of mammals, including human patients. It also is intended that the therapeutic agent and 5-(2,5-dimethyl phenoxy)-2,2-dimethylpetanoic acid, or a structural analog thereof, be administered as a composition comprising the therapeutic agent and 5-(2,5-dimethyl phenoxy)-2,2-dimethylpetanoic acid (or a structural analog thereof) and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water emulsion, and various types of wetting agents.

Methods of administration to mammals are well known to those of ordinary skill in the art and include, but are not limited to, administration orally, intravenously or parenterally. Administration of the compositions will be in an effective dosage. Administration may be effected continuously or intermittently such that the amount of the composition in the patient is effective.

In addition, the therapeutic agent may be administered at the same time as, or subsequent to, the administration of 5-(2,5-dimethyl phenoxy)-2,2-dimethylpentanoic acid, or a structural analog therof.

EXPERIMENTAL METHODS

Cells and Chemicals: J774 cells were grown in spinner culture in Dulbecco's modified Eagle medium (DMEM) containing 10% heat inactivated calf bovine serum, 100 unit/ml penicillin G and 100 µ/ml streptomycin (D10). Before experiments using penicillin, cells were grown in penicillin-free medium overnight. [$^{14}$C] Penicillin G was from New England Nuclear. [$^{3}$H] Norfloxacin was a gift from Merck, Sharpe, and Dohme Co. (New Jersey). Lucifer Yellow CH, lithium salt, was from Molecular Probes (Eugene, Oreg.). Probenecid and sulfinpyrazone were from Sigma (St. Louis, Mo.).

FIRST SERIES OF EXPERIMENTS

Materials and Methods

Measurement of Intracellular Lucifer Yellow: J774 cells were plated at 106 cells/well in 24-well tissue culture plates and cultured in D10 at 37° C. overnight. The cells were incubated in phosphate buffered saline with divalent cations (PBS) containing 0.5 mg/ml Lucifer Yellow, 5 mM ATP and other compounds, at 37° C. as indicated in the text. The wells were washed with cold phosphate buffered saline without divalent cations (PD) 3 times, and plates were immersed successively in three beakers containing 1,000 ml cold PD. The first beaker also contained 0.1% bovine serum albumin. The cells then were lysed in 0.05% Triton X-100, and fluorescence was measured in a fluorescence spectrophotometer using an excitation wavelength of 430 nm and an emission wavelength 540 nm. Total cell protein was measured by a modification of the Lowery method. (6) Results were expressed as ng Lucifer Yellow/mg protein.

[$^{14}$C]-Penicillin G Efflux from J774 cells: J774 cells were plated at 106 cells/well in 24-well tissue culture plates and incubated in D10 with neither penicillin nor streptomycin in the medium at 37° C. and 5% $CO_2$ overnight. The cells were incubated in PBS containing 0.5 µCi/ml [$^{14}$C] penicillin G and 5 mM ATP for 10 minutes before the loading was terminated by washing the cells with cold PD as described above. DMEM with or without 10 mM probenecid was added to the cells and the cells were incubated at 37° C. to 5% $CO_2$ for various time periods. At the end of each time point, the cells were washed with cold PD, the cells were lysed with 0.5% Triton X-100, radioactivity was measured in a scintillation counter, and protein was quantitated as above.

[$^{3}$H]-Norfloxacin Retention in J774 Cells: J774 cells were prepared as above. The cells were incubated in PBS with 1.5 µCi/ml [$^{3}$H] norfloxacin in the presence or absence of 10 mM probenecid for various lengths of time, washed and lysed. Cell-associated radioactivity and protein were quantitated as above.

SECOND SERIES OF EXPERIMENTS

Materials and Methods

L. monocytogenes strain 101035 was provided by Dr. D. Portnoy, Univ. of Pennsylvania, Philadelphia, Pa. The bacteria were grown in brain heart infusion broth (BHI) and on LB agar (Difco Laboratories, Inc., Detroit, Mich.) for analysis of MIC and MBC. Bacteria grown in BHI broth were suspended in DME+5% HICS media (Life Technologies, Inc., Grand Island, N.Y.) to insert J774 cells.

Tissue Culture Cells and Growth Medium

J774 macrophage-like cells were grown in DME containing 5% heat inactivated (56° C.×30 min) calf serum (HICS), penicillin (100 U/ml) and streptomycin (10 µg/ml). For experiments with L. monocytogenes, $10^6$ J774 cells were plated in 60 mm petri dishes (Corning Glass Works, Corning, N.Y.) in DME containing 5% HICS but without antibiotics and incubated overnight at 37° C. in the medium.

Extracellular Growth Assay

Minimum Inhibitory Concentration (MIC) of Norfloxacin

L. monocytogenes were inoculated into 1 ml of BHI broth and grown overnight in BHI broth to a density of approximately $10^9$ bacteria per ml, diluted to a concentration of $2\times10^3$ bacteria per ml in Brain Heart Infusion Broth, and 0.5 ml aliquots of this suspension were placed in separate tubes. Norfloxacin (NFX) at the indicated concentrations in 0.5 ml BHI broth was added to the tubes containing L. monocytogenes, and the bacteria were incubated overnight at 25° C., 30° C. and 35° C. The MIC of NFX for L. monocytogenes was determined by visual inspection (tubes without antibiotic, in which the bacteria grew contained a cloudy suspension).

Minimum Bacteriocidal Concentration (MBC)

10 µl of the contents of each sample from the MIC assay described above was plated on 10 cm plates containing 20 ml. LB, agar, and the plates were incubated overnight at 25° C., 30° C. and 35° C. The number of colonies were counted.

Inoculation and growth of L. monocytogenes in J774 cells

J774 cells grown in spinner culture were centrifuged for 5 min. at 1000 RPM. The cells were resuspended in fresh DME+5% HICS without antibiotics at a concentration of $2\times10^5$. 5 ml of this cell suspension was plated into each 60 mm Petri dish containing multiple 12×1 mm round coverslips (Fisher Scientific Co.) the evening before use to allow the cells to form monolayers on the coverslips. The cells were incubated overnight at 37° C.

L. monocytogenes was incubated overnight in BHI broth to a density of approximately $10^9$/ml in a shaker at 37° C. 1 ml of the bacterial suspension was sedimented in a microfuge tube (USA/Scientific Plastics, Ocala, Fla.) for 1 min at 8000 RPM. The supernatant was removed and the pellet was washed once in 1 ml of PBS at pH 7.4. The bacteria were then resuspended in 1 ml fresh DME+5% HICS, diluted in DME+5% HICS to a concentration of $2\times10^5$ bacteria per ml, and 5 ml of this suspension ($10^6$ bacteria total) was placed in each 60 mm dish containing a monolayer of J774 cells (infection ratio 1:1). The dishes were incubated at 35° C. for 60 minutes. The coverslip was then transferred to a new 60 mm petri dish containing 10 ml of pre warmed DME+5% HICS and 5 μg/ml of gentamicin. The cells were incubated in the gentamicin containing medium for 1 hr. at 35° C. to kill extracellular bacteria, as described by Portnoy et al. (9), at which time additional drugs were added as indicated below. One 60 mm dish received no addition (control). Other 60 mm dishes received Gemfibrozil (GFZ) (0.2 mM), and/or Norfloxacin (NFX) at 2, 4 or 8 μg per ml, as indicated. Drugs were added either separately or in combination to make four independent sets: No addition, GFZ alone, NFX alone, or GFZ+NFX. The cultures were further incubated at 35° C. Three coverslips containing the Listeria-infected J774 cells were harvested from each culture dish at 2 hours after infection and at 2 hour intervals thereafter. The number of bacteria in the J774 cells on each cover slip was determined by depositing each coverslip into 5 ml of sterile distilled water in a 15 ml Falcon tube. The tubes were vortexed for 15 sec. to lyse the infected cells and 10 or 50 μL of each Listeria-containing solution was plated onto 10 cm dishes containing LB agar. The LB agar plates were incubated at 37° C. overnight, the bacterial colonies were counted, and the number of bacteria per cover slip was calculated from the number of colonies on the agar. Every data point represents the average of the number of bacterial colonies recovered from three coverslips.

RESULTS

FIRST SERIES OF EXPERIMENTS

Figure 1:
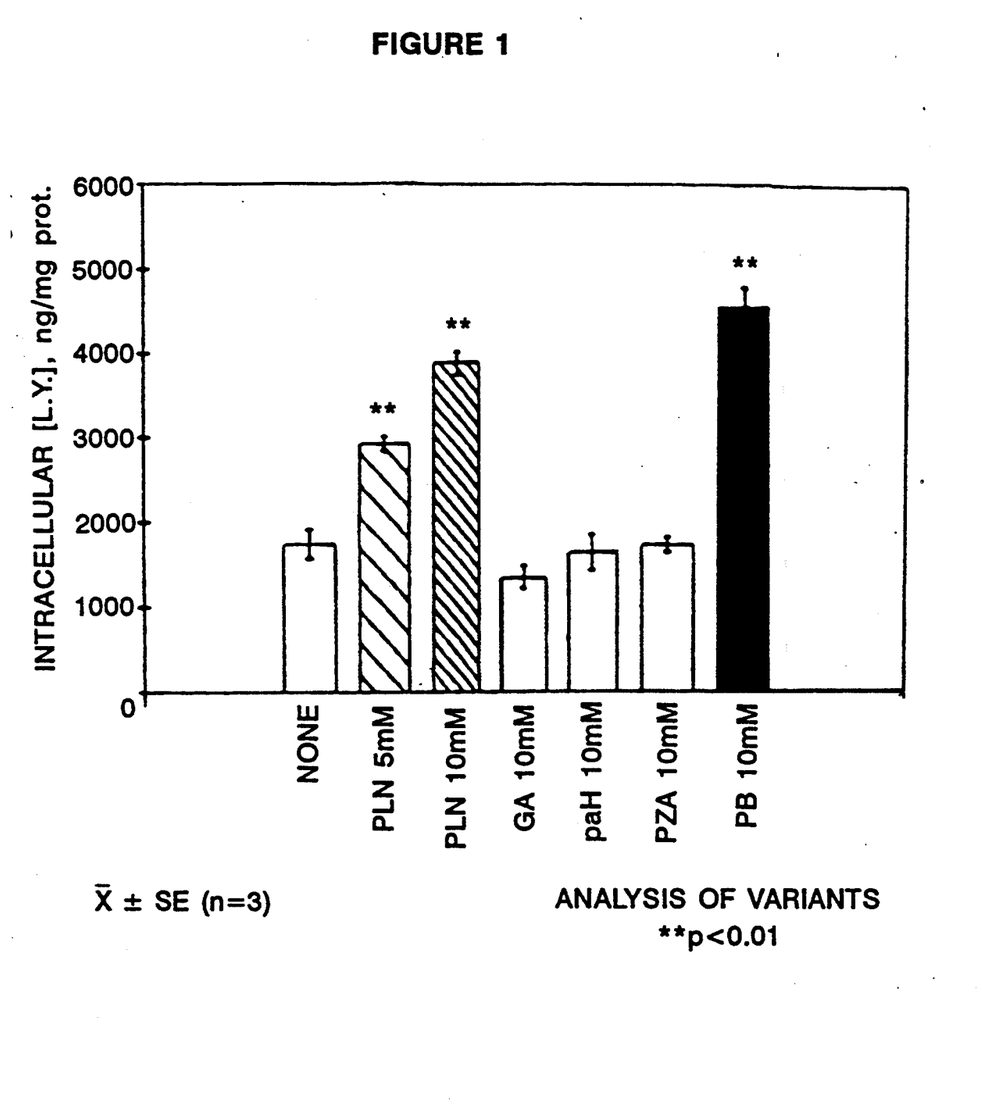

The organic anion transporter of J774 cells limits intracellular accumulation of Lucifer Yellow during ATP permeabilization Extracellular ATP$^4$ permeabilizes the plasma membrane of J774 cells to small molecules (<900 daltons) such as Lucifer Yellow (7). When J774 cells are incubated in medium containing Lucifer Yellow and ATP, the dye rapidly permeates the cytoplasmic matrix of the cells. However, after Lucifer Yellow enters the cell cytoplasm, most of the dye is secreted into the extracellular medium by probenecid-inhibitable organic anion transporters. (1) Inhibition of the organic anion transporters therefore would be expected to increase the intracellular accumulation of Lucifer Yellow during ATP permeabilization. It was found that if 5-10 mM probenecid is present in the medium in addition to Lucifer Yellow and ATP, the intracellular retention of Lucifer Yellow in the J774 cells was increased 2.5 fold (FIG. 1). Analysis of the effects of probenecid on variant cell lines that secrete Lucifer Yellow more efficiently than do the wild-type J774 cells shows that probenecid does not effect ATP permeabilization. Therefore, the above results show that the organic anion transporters significantly limit the intracellular retention of Lucifer Yellow during ATP permeabilization.

Penicillin G is a substrate for the organic anion transporter that secretes Lucifer Yellow An assay to identify competitive inhibitors of the organic anion transporters that mediate the secretion of Lucifer Yellow was developed. It was reasoned that any substrate of the organic anion transporter small enough to enter the cells through ATP-induced pores, when added together with Lucifer Yellow during ATP permeabilization, would compete with Lucifer Yellow for efflux and cause higher intracellular accumulation of Lucifer Yellow. This assay was used to determine whether various substrates for other organic anion transporters competed with Lucifer Yellow for secretion by J774 cells. Gluconic acid, pyrazinamide, paraaminohippurate and several other organic anions had no effect on the intracellular accumulation of Lucifer Yellow during ATP permeabilization. In contrast, penicillin G was able to increase Lucifer Yellow retention in a dose-dependent manner (FIG. 1).

Penicillin G also reduced the rate of Lucifer Yellow afflux after both compounds were introduced into J774 cells simultaneously by ATP-mediated permeabilization. Cells were incubated in D10 containing 0.5 mg/ml Lucifer Yellow and 5 mM ATP with or without 10 mM penicillin G. The cells were then washed and incubated in fresh medium at 37° C. At intervals, the cells were viewed by fluorescence microscopy. When 10 mM penicillin was present in the medium while Lucifer Yellow was introduced into the cells, more Lucifer Yellow was present in the cytoplasmic matrix of the cells at subsequent times.

Figure 2:
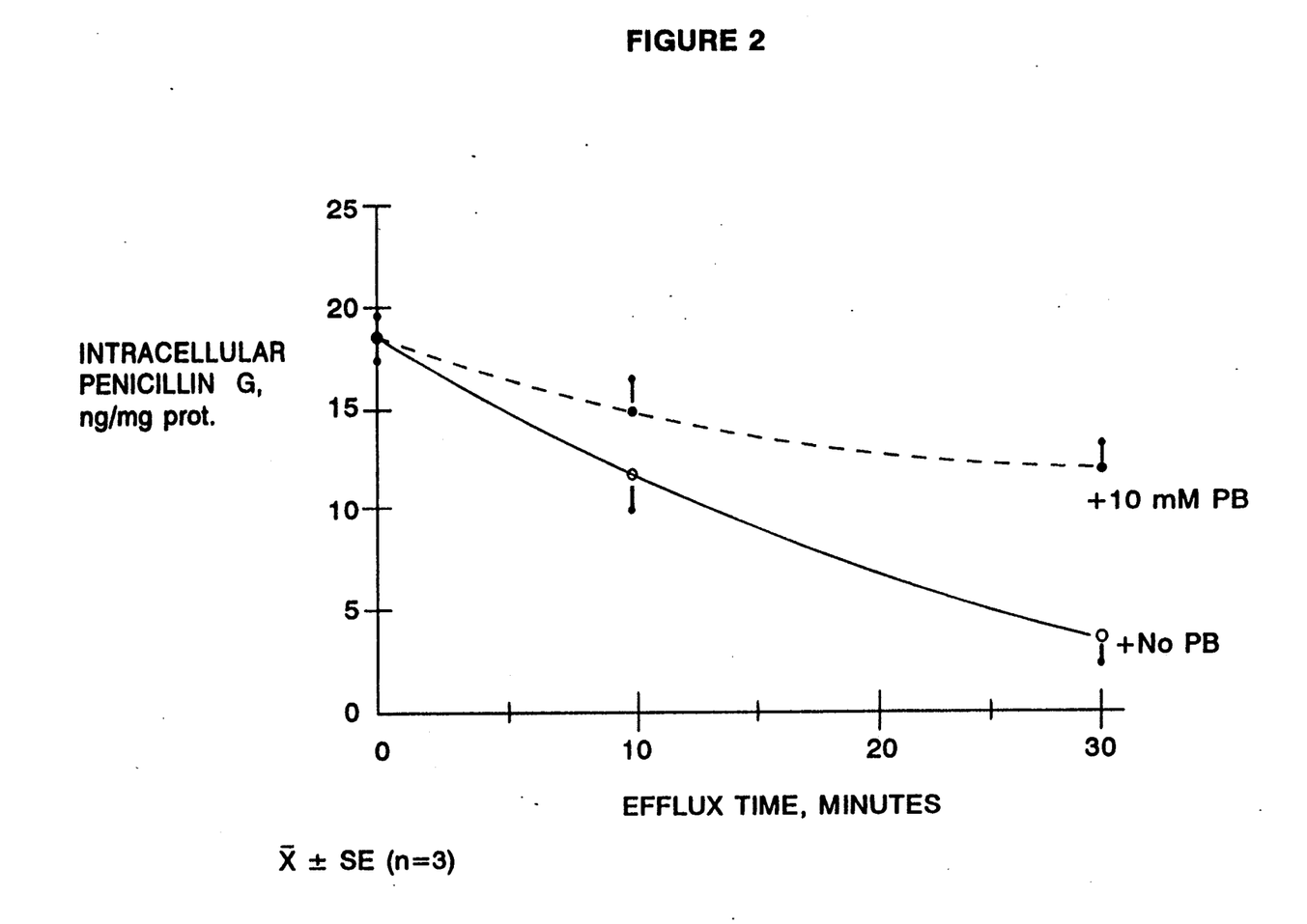

To demonstrate directly that penicillin is a substrate of the organic anion transporter, [$^{14}$C] penicillin G was loaded into the J774 cells by ATP permeabilization, the cells were washed to reseal the plasma membrane, the cells were incubated in DMEM at 37° C., and the amount of radiolabel was measured in the cells at intervals. After 30 minutes about 80% of penicillin originally inside the cells was secreted into the medium (FIG. 2). In the presence of 10 mM probenecid, only 37% of the intracellular penicillin was secreted from the cells by this time. The above studies show that penicillin is a substrate for the same organic anion transporters that secrete Lucifer Yellow from the cytoplasmic matrix of J774 cells into the extracellular medium.

It was then questioned whether penicillin G was taken up by J774 cells from the extracellular medium, and whether this uptake was affected by organic anion transporters. In these experiments, adherent J774 cells were incubated in medium containing [$^{14}$C] penicillin G, the cells were washed, and intracellular radiolabel was measured. However, the total amount of intracellular radiolabel was so small that it could not be readily detected in adherent cells even in the presence of 10 mM probenecid (data not show). Therefore, the water soluble molecule penicillin G was not taken up by J774 cells sufficiently well in the absence of ATP-induced permeabilization to determine whether inhibition of organic anion transporters affected its intracellular accumulation. This result is consistent with the published literature.

Uptake of norfloxacin is enhanced by probenecid

Figure 3:
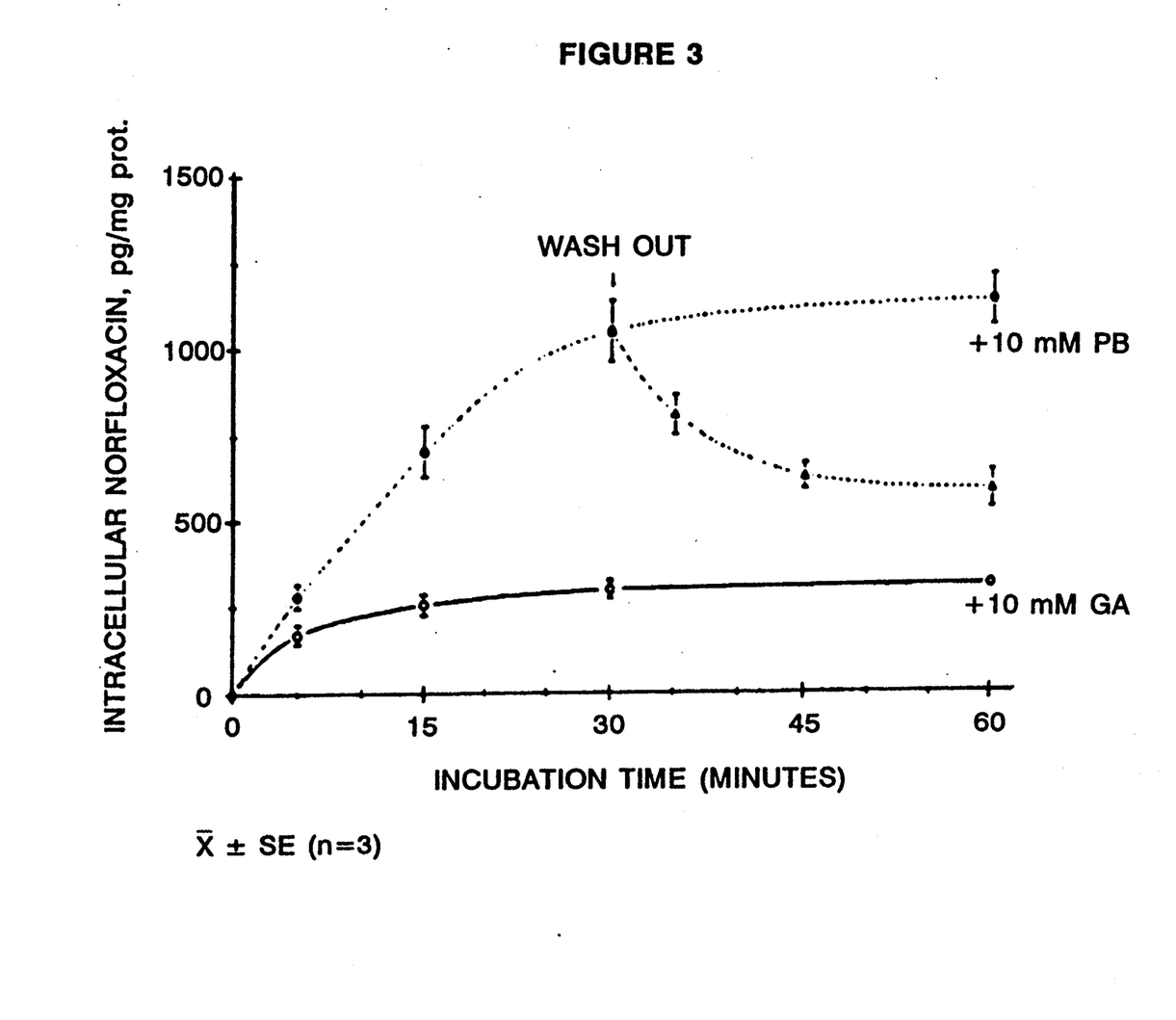

Norfloxacin, a quinoline antibiotic with a broad spectrum of antimicrobial activity, is also an organic anion. Unlike Lucifer Yellow and penicillin G, which do not readily enter cells in the absence of ATP$^4$, norfloxacin is lipid soluble and crosses cellular membranes readily. Thus, it was possible to assess norfloxacin secretion without permeabilizing the plasma membrane with ATP$^4$. J774 cells were incubated in medium containing [3H]norfloxacin in the presence of either 10 mM probenecid or 10 mM gluconic acid (control) and intracellular radiolabel content was measured at intervals (FIG. 3). It was found that probenecid enhanced the intracellular accumulation of norfloxacin 3-4 fold compared to cells incubated with gluconic acid. Gluconic acid did not affect the intracellular norfloxacin concentration as compared with the cells incubated with only norfloxacin in PBS (data not shown). In the absence of probenecid, the intracellular norfloxacin concentration had already reached its plateau after a 10 minute incubation; in the presence of 10 mM probenecid, the intracellular norfloxacin concentration reached plateau at 30 minutes.

The effect of probenecid was reversible; the J774 cells were incubated with 1.5 µCi/ml [³H] norfloxacin and 10 mM probenecid in PBS for 30 minutes; then in some samples the cells were washed and bathed in medium containing only 1.5 µCi/ml [³H] norfloxacin in PBS. After probenecid was removed from the medium, there was a rapid efflux of norfloxacin from the cells followed by a steady state in which no further loss of antibiotic from the cells occurred (FIG. 3). The amount of [³H] norfloxacin that remained within the cells at this time was twice that of the cells which had never been incubated in probenecid.

Figure 4A:
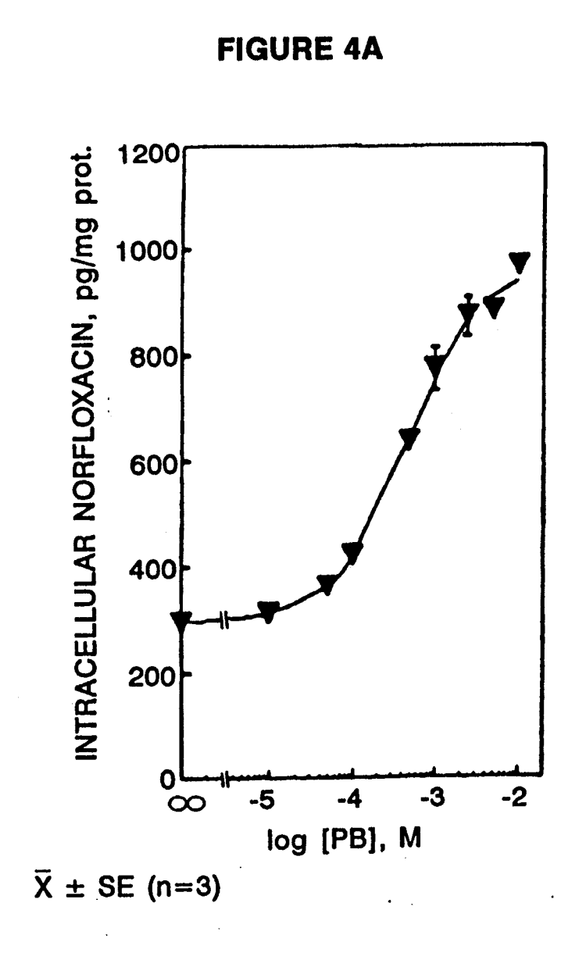
FIG. 4. Dose-response relationships for (a) probenecid and (b) sulfinpyrazone to increase intracellular retention of norfloxacin. J774 cells were incubated with [$^3$H] norfloxacin and either probenecid or sulfinpyrazone at different concentrations for 30 minutes. The cells were washed, lysed, and radiolabel was quantitated as described. The results show averages of three separate experiments each done in triplicates, and their standard errors.
Figure 4B:
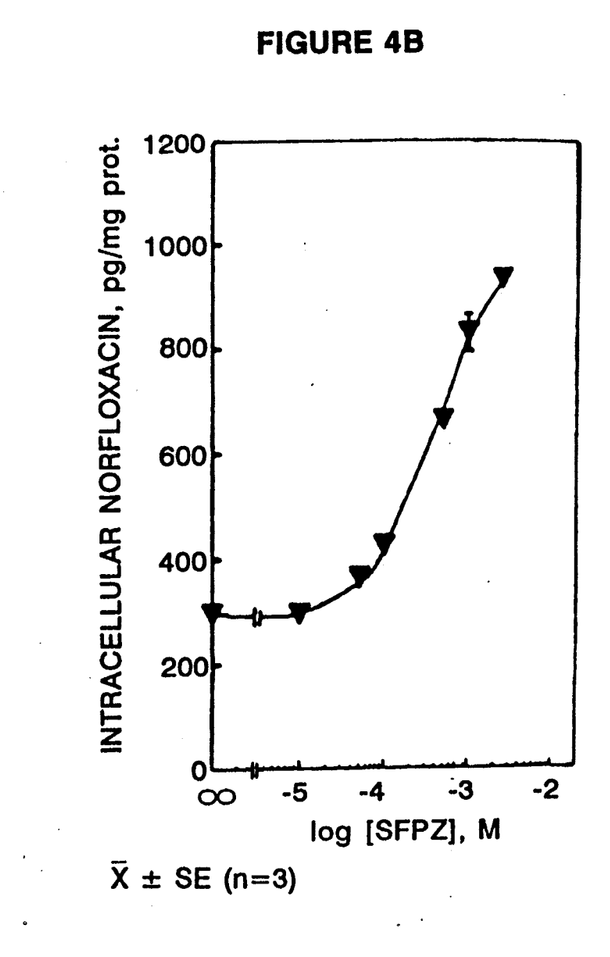

Probenecid enhanced the intracellular retention of norfloxacin with an $Ed_{50}$ of 0.5 mM (FIG. 4a); the $ED_{50}$ for sulfinpyrazone, another organic anion transport inhibitor, was essentially the same as that for probenecid (FIG. 4b). Concentrations of sulfinpyrazone greater than 2.5 mM were toxic to the cells.

Figure 5:
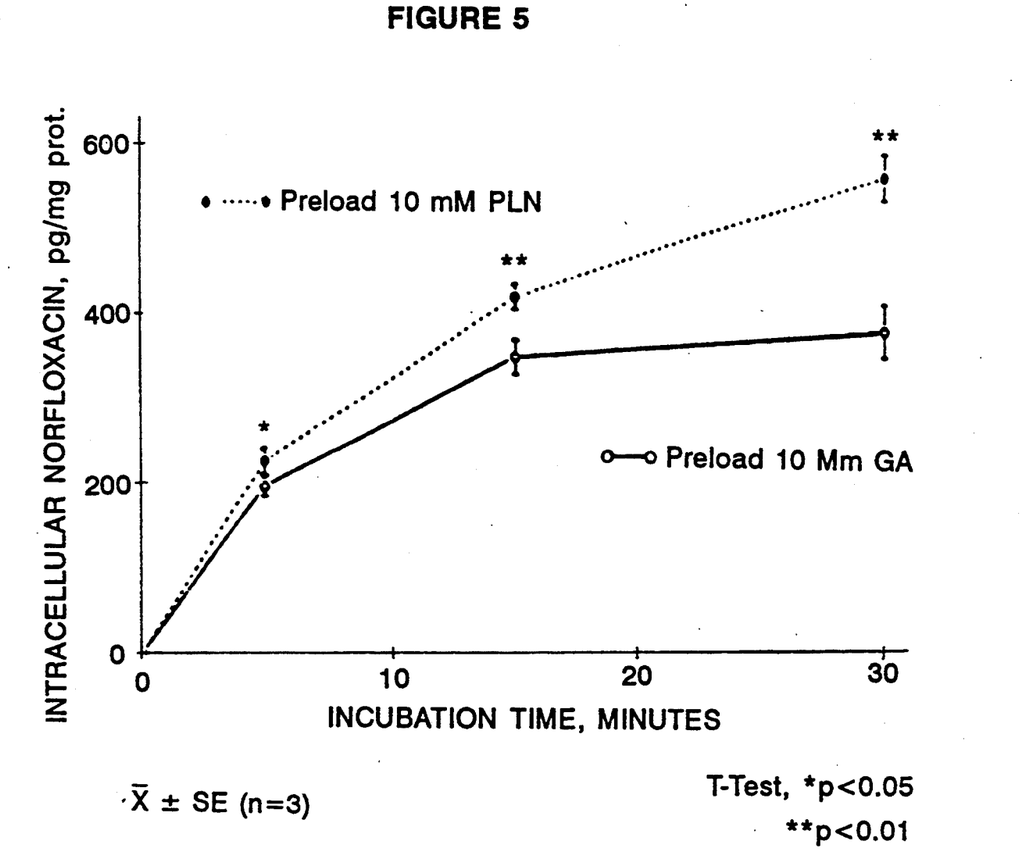
FIG. 5. Effect of preloading penicillin or gluconic acid on intracellular retention of $^3$H-NFX in J774 cells. J774 cells were preloaded with either 10 mM penicillin or 10 mM gluconic acid by ATP-permeabilization. Cells were then incubated with [$^3$H] norfloxacin in PBS, and the amount of radiolabel was measured in the cells at intervals.
Figure 6A:
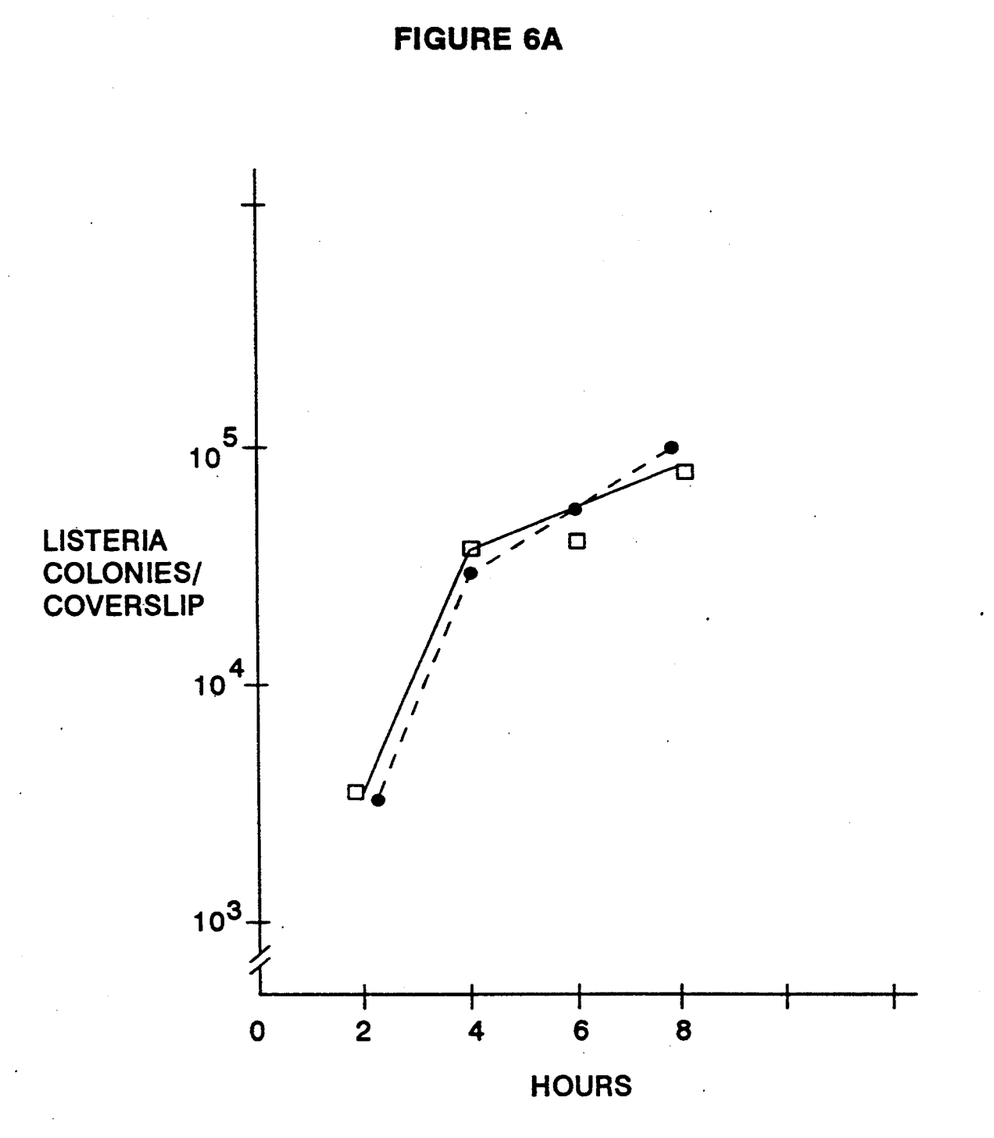
FIG. 6A. Intracellular growth of Listeria monocytogenes in J774 cells in the presence of 0.2 mM GFZ (open circles) or in the absence of GFZ (filled circles). The intracellular growth assays were performed as described in Materials and Methods (second series of experiments) which follow. Note that GFZ has no effect on the rate or extent of growth of Listeria monocytogenes.
Figure 6B:
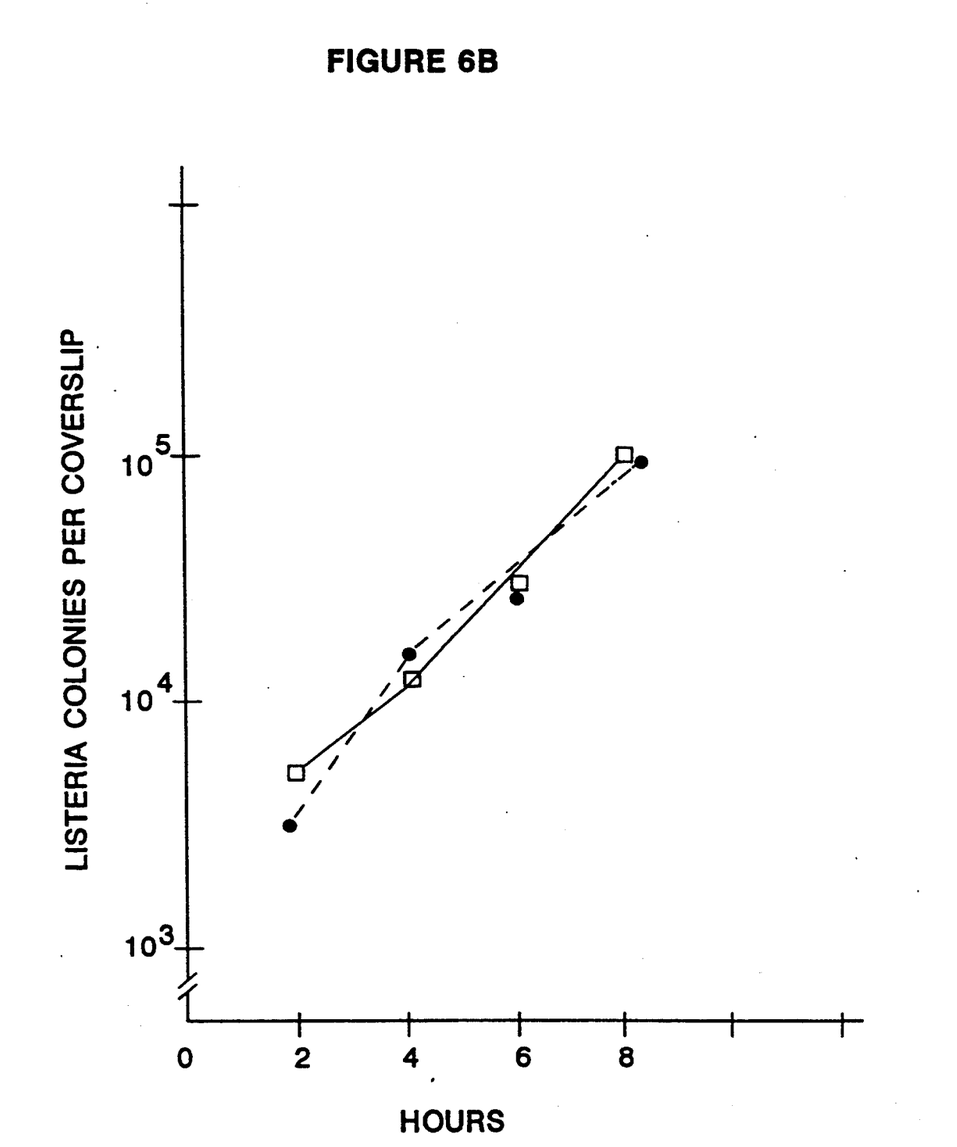
FIG. 6B. Repetition of the experiment of FIG. 6A.
Figure 7:
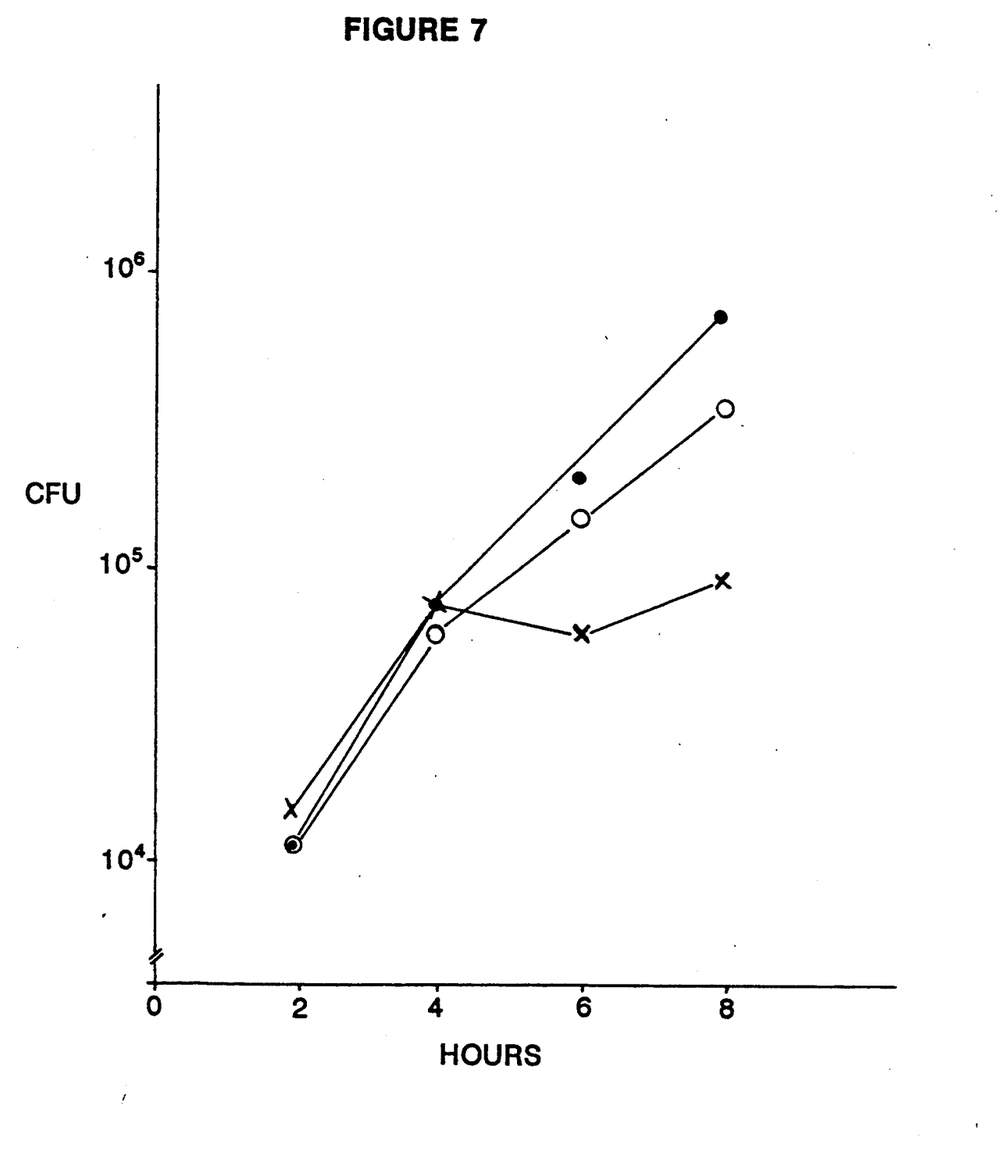
FIG. 7. Intracellular growth of Listeria monocytogenes in J774 cells under three different conditions: 0.2 mM GFZ (open circles), 2 ug/ml NFX (filled circles) and 0.2 mM GFZ+2 ug/ml NFX (X's). The intracellular growth assays were performed as described in Materials and Methods (second series of experiments) which follow. Note that 2 ug/ml NFX has little inhibitory effect on growth of Listeria while the same concentration of NFX causes marked inhibition of growth when used in combination with 0.2 mM GFZ.
Figure 8:
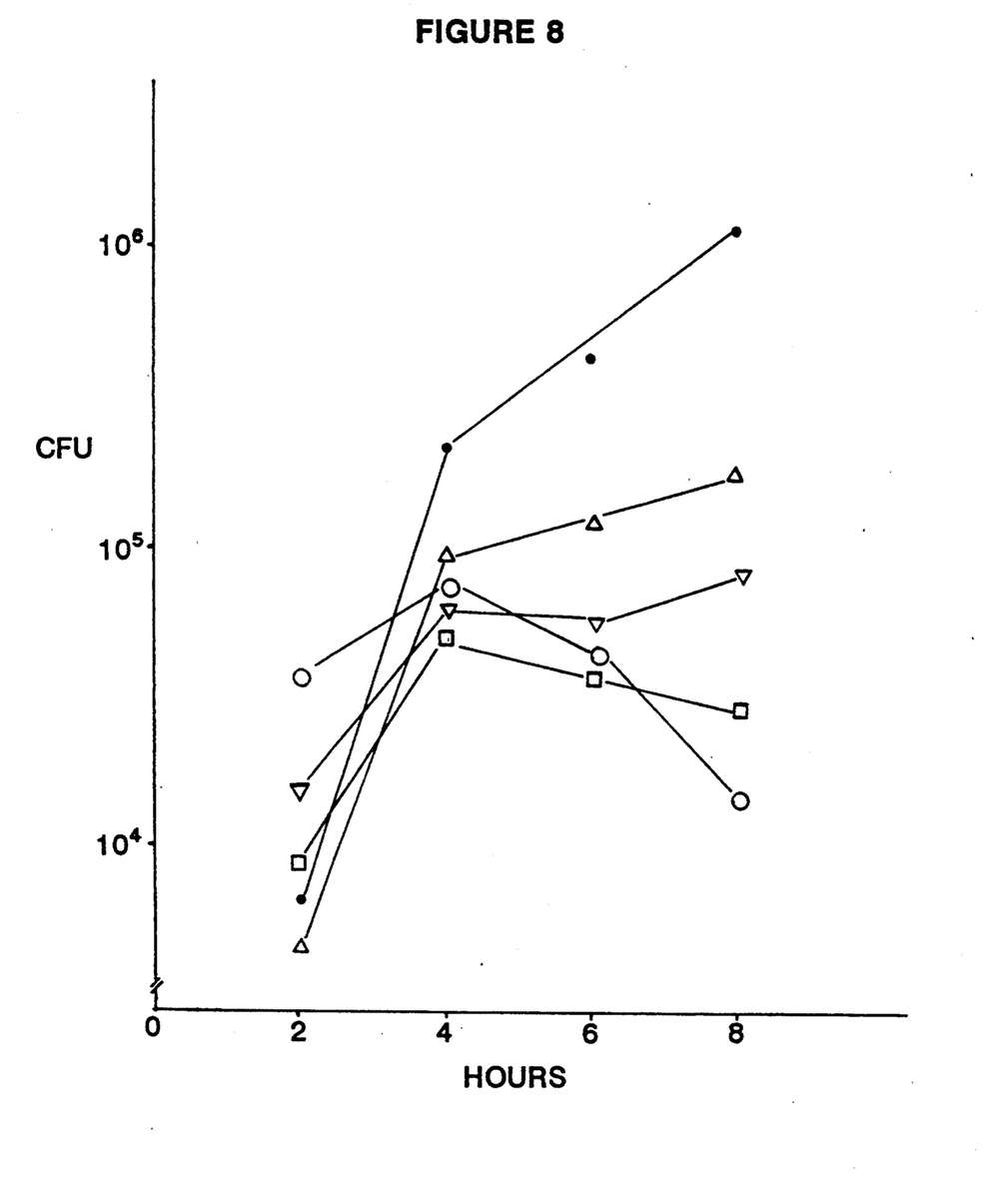
FIG. 8. Intracellular growth of Listeria monocytogenes in J774 cells under five different conditions: 0.2 mM GFZ (filled circles), 4 ug/ml NFX (open triangles), 0.2 mM GFZ+4 ug/ml NFX (open squares), 8 ug/ml NFX (inverted triangles) and 0.2 mM GFZ+8 ug/ml NFX (open circles). The intracellular growth assays were performed as described in Materials and Methods (second series of experiments) which follow. Note that there was marked inhibition of intracellular growth of Listeria monocytogenes in the presence of 4 ug/ml NFX alone, but this inhibition was markedly potentiated by the addition of 0.2 mM GFZ. Note that 8 ug/ml NFX had a bacteriostatic effect while addition of 0.2 mM GFZ plus 8 ug/ml NFX led to a bactericidal effect on intracellular Listeria monocytogenes.

It also was determined whether penicillin and norfloxacin compete for the same efflux pathway in J774 cells. J774 cells were preloaded with either 10 mM penicillin or 10 mM gluconic acid by ATP-permeabilization, cells then were incubated with [³H] norfloxacin in PBS, and the amount of radiolabel was measured in the cells at intervals as above. In the cells that had been preloaded with penicillin, there was a significant increase in accumulation of [³H] norfloxacin compared with cells that had been preloaded with gluconic acid at the same concentration (FIG. 5). Together with the above studies, this result indicates that norfloxacin and penicillin are transported by the same organic anion transporter in macrophage cell membrane.

SECOND SERIES OF EXPERIMENTS

Gemfibrozil Inhibits Organic Anion Secretion and Enhances Norfloxacin Accumulation in J774 Macrophage-like Cells.

Mouse macrophages and J774 cells possess organic anion transporters that promote the secretion of water-soluble, membrane-impermeant, anionic fluorescent dyes such as Lucifer Yellow (1) and antimicrobial agents such as penicillin and Norfloxacin (NFX) (10) from the cells' cytoplasm into the surrounding medium. Probenecid (PB) and sulfinpyrazone at concentrations of 2-5 mM block secretion of these substances, and thereby enhance their retention or accumulation within J774 cells. In an effort to identify more potent organic anion transport inhibitors, a number of compounds using secretion of Lucifer Yellow from J774 cells were screened. Gemfibrozil (GFZ), a fibric acid used to lower blood lipids, inhibited Lucifer Yellow secretion by J774 cells at a ten-fold lower concentration than PB. GFZ also enhanced the intracellular accumulation of [³H]NFX with an ED50 of 15 µM, which is 30-fold lower than the ED50 of PB or sulfinpyrazone in enhancing [3H]NFX accumulation by J774 cells. Thus GFZ may be useful in enhancing the intracellular accumulation of fluoroquinolone antibiotics, and other anionic antibiotics and drugs that are membrane-permeant. These findings also suggest additional mechanism(s) by which fibric acids may affect blood lipids.

Inhibition of Organic Anion Transport in J774 Macrophage-like Cells Potentiates the Ability of Norfloxacin to Inhibit the Intracellular Growth of Listeria monocytogenes in These Cells Listeria monocytogenes (LM) grows intracellularly in J774 cells (9). Addition of 2 µg/ml Norfloxacin (NFX) to the medium of LM-infected J774 cells slowed intracellular growth of these bacteria. Addition of 4 or 8 µg/ml of Norfloxacin (NFX) to the medium of LM-infected J774 cells was bacteriostatic. In contrast, 4 µg/ml NFX blocked growth of LM inoculated into brain-heart infusion broth and 8 µg/ml NFX was bacteriocidal for LM in this medium (MBC). Gemfibrozil (GFZ) (0.2 mM) inhibits organic anion secretion by J774 cells, and thereby enhances intracellular accumulation of NFX four-fold. GFZ (0.2 mM) does not inhibit growth of LM in J774 cells. However, when LM-infected J774 cells were incubated in medium containing 2 or 4 µg/ml NFX and 0.2 mM GFZ, intracellular growth of LM was inhibited. Incubation of LM-infected J774 cells in medium containing 8 µg/ml NFX and 0.2 mM GFZ was bacteriocidal for intracellular LM. These findings indicate that GFZ potentiates the action of NFX on intracellular LM; and suggest that GFZ could be used clinically to potentiate the effects of fluoroquinolones and other cell permeant anionic antibiotics against intracellular bacterial pathogens.

In vivo ability of gemfibrozil to potentiate the ability of antibiotics to protect against bacterial infections Listeria monocytogenes is a facultative intracellular pathogen that causes a severe infection of mice. Mice inoculated intravenously with a sublethal dose of Listeria show progressive growth of this organism in their liver and spleen. Mice inoculated with a sublethal dose of Listeria intraperitoneally show growth of Listeria in their peritoneal macrophages, with subsequent spread to liver and spleen. In all instances, the number of Listeria in each organ or body site can be enumerated by sacrificing the mouse, homogenizing the organ, and plating dilutions of the homogenate on nutrient agar. By counting the number of Listeria clones on the agar, the number of bacteria in the organ or tissue extract can be determined. Administration of an antibiotic, such as Norfloxacin, to the mice shortly after their inoculation with Listeria slows the rate of growth of these bacteria, reduces the number of bacteria that eventually reach the liver and spleen, and thereby speeds recovery of the mice from the infection. The administration of gemfibrozil together with norfloxacin to mice inoculated with Listeria can evaluate the inhibitory effect of this antibiotic on Listeria growth and the potentiating effect of gemfibrizol. Specifically, a number of viable Listeria in the liver, spleen, and peritoneal cavity of Listeria-infected mice can be measured wherein the mice are given: 1. No treatment. 2. Various doses of gemfibrozil alone. 3. Various doses of norfloxacin alone. 4. gemfibrozil and norfloxacin in combination.

Discussion

In the first series of studies, it was shown that penicillin G and norfloxacin, antibiotics that belong to two of the most important groups of antibacterial agents, are rapidly removed from the cytoplasmic matrix of macrophage cells by organic anion transporters in the cell membrane. Organic anion transporters were previously identified in macrophages by their ability to sequester fluorescent dyes such as Lucifer Yellow from the cytoplasmic matrix of the cells into endosomes and to secrete the dyes into the extracellular medium. (1, 2) As in the previous studies in which Lucifer Yellow was examined as the substrate of the transporter, probenecid and sulfinpyrazone inhibited the efflux of these antibiotics as well.

Penicillin G is hydrophilic and did not attain a measurable concentration in the cytoplasmic matrix of adherent macrophages in these studies. Only when [$^{14}$C] penicillin G was introduced into the macrophages by ATP-mediated permeabilization, was the effect of probenecid on membrane transport apparent: penicillin was rapidly secreted into the extracellular medium. Penicillin G therefore behaves similarly to Lucifer Yellow in these respects.

The studies of penicillin transport confirm that there is an apparent "sidedness" to the organic anion transporter, that is, in intact cells the transporter secretes substrates from the cytoplasmic matrix but does not accumulate extracellular organic anions. These data also are consistent with previous studies of Lucifer Yellow transport in intact cells (1) and in subcellular organelles. Because under "normal" conditions, in this case in the absence of ATP-induced permeabilization, penicillin does not enter cells, organic anion transporters may not have a major influence on the intracellular disposition of membrane-impermeant drugs unless these drugs can enter cells by some other pathway.

Norfloxacin is much more lipid soluble than is penicillin G, and accumulates within the cytoplasmic matrix of macrophages when the cells are incubated in medium containing norfloxacin. When J774 cells were incubated in medium containing [$^3$H] norfloxacin and either probenecid or sulfinpyrazone, a marked increase was seen in the intracellular accumulation of radiolabel. Therefore, in the absence of probenecid or sulfinpyrazone, the intracellular accumulation of radiolabeled norfloxacin is limited by concomitant secretion of the drug. In addition to norfloxacin, probenecid also enhances the intracellular accumulation of membrane-permeant esterified derivatives of fluorescent dyes such as fura-2 acetoxymethyl ester (3) and carboxyfluorescein diacetate (J. Swanson, personal communication). Thus, organic anion transport blockers can increase the cytosolic concentration of a variety of therapeutic agents that are organic anions and also are lipophilic or otherwise gain access to the cytoplasmic matrix.

When penicillin G is introduced into the cells by ATP-induced permeabilization, the drug initially must be in the cytoplasmic matrix (except for the small fraction of the drug that is taken up by pinocytosis). As with Lucifer Yellow, that penicillin G may also be sequestered within endosomes at the same time that it is secreted into the medium.

In the absence of probenecid, norfloxacin is taken up both by pinocytosis and by diffusion across the plasma membrane and is secreted back into the medium by the organic anion transporters, and presumably is also sequestered within the endocytic compartment. When organic anion transport is inhibited by probenecid, norfloxacin accumulation is enhanced because the drug is not simultaneously secreted from the cells, and thus, accumulation of norfloxacin within endosomes and lysosomes is inhibited at the same time. This also is the case with fura-2 (3). It is therefore possible that complete inhibition of organic anion transporters paradoxically decreases drug concentration within endocytic compartments and phagosomes at the same time that it increases the total intracellular concentration of a drug.

When probenecid was removed from the medium of cells that had been incubated in both probenecid and norfloxacin, after an initial period of rapid afflux of the quantity of intracellular norfloxacin remained higher than in cells that had never been exposed to probenecid. Thus, when compared to the intracellular fate of fluorescent dyes, it is concluded that this represents increased accumulation of norfloxacin within the endocytic compartment, ultimately within lysosomes.

These findings may have important implications for the efficacy of antibiotics in intracellular infections. A number of bacterial pathogens including Salmonella, Brucella, Listeria, Legionella, and Mycobacteria, are able to survive in macrophages after being ingested. Many factors influence the ability of antimicrobials to eradicate infections with intracellular pathogens. These include among others the intracellular location of the organism, the concentration of antibiotic in that location, and the sensitivity of the organism to the particular agent under the conditions that prevail there. In some instances, antibiotics that are effective against a pathogen in vitro fail to arrest infections with these organism in vivo. Some organisms, such as Listeria, avoid the antimicrobial responses of phagocytes by escaping from the phagocytic vacuole and growing within the cytoplasmic matrix. These findings suggest that organic anion transport blockers may be useful in these instances because they increase the intracellular antibiotic concentration in this compartment.

It is also possible to increase the concentration of antibiotics within phagosomes by delivering more antibiotic to the phagocytes and subsequently reversing inhibition of organic anion transport. Therefore, a short-half-life organic, anionic transport inhibitor such as Caronamide is a useful adjunct to antibiotic therapy of intracellular pathogens by selectively increasing the antibiotic concentration in phagosomes (8).

Finally, based on their similar chemical structures, other beta-lactam antibiotics such as semisynthetic penicillins and cephalosporins, and other quinoline antibiotics such as ciprofloxacin and some quinoline compounds that have potential antitumor activities, may also be transported from the cells by organic anion transporters. However, since among these compounds structural distinctions do exist, it is possible that these antibiotics are transported at a significantly different degree, so that they may be concentrated in different cellular compartments. Under different clinical conditions, the use of an antibiotic that accumulates in a particular cellular compartment may be beneficial. By considering the effect of organic anion transporters or other membrane transporters on drug distribution, it is possible to design more effective therapies for intracellular infections or other pathologic processes.

In addition to J774 cells and primary mouse macrophages, organic anion transporters also have been identified in primary mouse macrophages (1), N2A neuroblastoma cells, PC12 cells (3) and Chinese hamster ovary cells.

References
1. Steinberg, T. H., A. S. Newman, J. A. Swanson, and S. C. Silverstein, 1987. Macrophages possess probenecid-inhibitable organic anion transporters that remove fluorescent dyes from the cytoplasmic matrix. J. Cell Biol. 105:2695–2702.
2. Steinberg, T. H., J. A. Swanson, and S. C. Silverstein, 1988. A prelysosomal compartment sequesters membrane-impermeant fluorescent dyes from the cytoplasmic matrix of J774 macrophages. J. Cell Bio. 107: 887–896.
3. Di Virgilio, F., C. Fasolato, and T. H. Steinberg, 1988. Inhibitors of membrane transport system for organic anions block fura-2 excretion from PC12 and N2A cells. Biochem. J. 256:959–963.

4. Endicott, J. A., and V. Ling, 1989. The biochemistry of P-glycoprotein-mediated multidrug resistance. Annu. Rev. Biochem. 58: 137–171.

5. Slovak, M. L., L. Lothstein, S. B. Horwitz, and J. M. Trent, 1988. Molecular/cytogenetic alterations accompanying the development of multidrug resistance in the J774.2 murine cell line. Leukemia 2: 453–458.

6. Lowry, O. H., N. J. Rosebrough, A. L. Farr, and R. J. Randall, 1951. Protein measurement with the folin phenol reagent. J. Biol. Chem. 193:265–275.

7. Buisman, H. P., T. H. Steinberg, J. Fischbarg, S. C. Silverstein, S. A. Vogelzang, C. Ince, D. L. Ypey, and P. C. J. Leijh. 1988. Extracellular ATP induces a large, nonselective, conductance in macrophage plasma membranes. Proc. Natl. Acad. Sci. USA. 85:7988–7992.

8. Beyer, K. H., A. K. Miller, H. F. Russo, E. A. Patch, and W. F. Verwey, 1947. The inhibitory effect of caronamide on the renal elimination of penicillin. Am. J. Physiol. 149:355–368.

9. Portnoy, D., P. S. Jacks, and D. J. Hinrichs (1988) Role of Hemolysin for the Intracellular Growth of Listeria Monocytogenes. J. Exp. Med. 167: 1459–1471.

10. Cao, C. et al., 1990. Clin. Res. 38:364A.

What is claimed is:

1. A method to enhance intracellular accumulation in mammalian cells of a hydrophilic, anionic antibiotic which cannot normally accumulate in such cells selected from the group consisting of:
   beta-lactam antibiotics; and
   quinolone antibiotics,
which comprises contacting the cells with the antibiotic and with 5-(2,5-dimethylphenoxy)-2,2-dimethylpentanoic acid, or a structural analog thereof, in an amount effective to block transport of the antibiotic from the cells causing intracellular accumulation of the antibiotic in the cells.

2. The method of claim 1, wherein the beta-lactam antibiotic is selected from the group consisting of penicillins and cephalosporins.

3. The method of claim 1, wherein the quinolone is ciprofloxacin.

4. The method of claim 1, wherein the quinolone is norfloxacin.

5. The method of claim 1, wherein the contacting with the antibiotic and with the 5-(2,5-dimethylphenoxy)-2,2-dimethylpentanoic acid, or a structural analog thereof is sequential.

6. The method of claim 1, wherein the contacting with the antibiotic and with the 5-(2,5-dimethylphenoxy)-2,2-dimethylpentanoic acid, or a structural analog thereof is simultaneous.

7. An improved therapeutic method which comprises administering to a mammal an antibiotic selected from the group consisting of:
   beta-lactam antibiotics; and
   quinolone antibiotics,
and 5-(2,5-dimethylphenoxy)-2,2-dimethylpentanoic acid, or a structural analog thereof, in an amount effective to improve the efficacy of the antibiotic.

8. The method of claim 7, wherein the mammal is a human.

9. The method of claim 7, wherein the beta-lactam antibiotic is selected from the group consisting of penicillins and cephalosporins.

10. The method of claim 7, wherein the quinolone is ciprofloxacin.

11. The method of claim 7, wherein the quinolone is norfloxacin.

12. The method of claim 7, wherein the administering of the antibiotic and the 5-(2,5-dimethylphenoxy)-2,2-dimethylpentanoic acid, or a structural analog thereof is sequential.

13. The method of claim 7, wherein the administering of the antibiotic and the 5-(2,5-dimethylphenoxy)-2,2-dimethylpentanoic acid, or a structural analog thereof is simultaneous.

14. A pharmaceutical composition comprising a hydrophilic anionic antibiotic which cannot normally accumulate in mammalian cells, selected from the group consisting of:
   beta-lactam antibiotics: and
   quinolone antibiotics,
and 5-(2,5-dimethylphenoxy)-2,2-dimethylpentanoic acid, or a structural analog thereof, and a pharmaceutically acceptable carrier.

15. The pharmaceutical composition of claim 14, wherein the beta-lactam antibiotic is from the group consisting of penicillins and cephalosporins.

16. The pharmaceutical composition of claim 14, wherein the quinolone is ciprofloxacin.

17. The pharmaceutical composition of claim 14, wherein the quinolone is norfloxacin.

18. A method of treating an intracellular bacterial infection which comprises contacting the infected cell with an effective amount of an antibiotic selected from the group consisting of:
   beta-lactam antibiotics; and
   quinolone antibiotics,
and with an effective amount of 5-(2,5-dimethylphenoxy)-2,2-dimethylpentanoic acid, or a structural analog thereof, effective to treat an intracellular bacterial infection.

19. The method of claim 18, wherein the beta-lactam antibiotic is selected from the group consisting of penicillins and cephalosporins.

20. The method of claim 18, wherein the quinolone is ciprofloxacin.

21. The method of claim 18, wherein the quinolone is norfloxacin.

22. The method of claim 18, wherein the contacting with the therapeutic agent and with the 5-(2,5-dimethylphenoxy)-2,2-dimethylpentanoic acid, or a structural analog thereof, is sequential.

23. The method of claim 18, wherein the contacting with the therapeutic agent and with the 5-(2,5-dimethylphenoxy)-2,2-dimethylpentanoic acid, or a structural analog thereof, is simultaneous.

24. A method of claim 18, wherein the intracellular bacterial infection is an infection by Listeria, Tuberculosis, Mycoplasma, Legionella, Leprosy, Brucella or Salmonella.

* * * * *